United States Patent
Nerdinger et al.

(10) Patent No.: US 7,256,194 B2
(45) Date of Patent: *Aug. 14, 2007

(54) COMPOUNDS THAT INHIBIT FACTOR XA ACTIVITY

(75) Inventors: Sven Nerdinger, München (DE); Thilo Fuchs, München (DE); Katrin Illgen, München (DE); Robert Eckl, München (DE)

(73) Assignee: Morphochem, Munich (DE)

( * ) Notice: Subject to any disclaimer, the term of this patent is extended or adjusted under 35 U.S.C. 154(b) by 246 days.

This patent is subject to a terminal disclaimer.

(21) Appl. No.: 10/468,975

(22) PCT Filed: Feb. 22, 2002

(86) PCT No.: PCT/EP02/01934

§ 371 (c)(1),
(2), (4) Date: Nov. 20, 2003

(87) PCT Pub. No.: WO02/068390

PCT Pub. Date: Sep. 6, 2002

(65) Prior Publication Data

US 2004/0082547 A1    Apr. 29, 2004

(30) Foreign Application Priority Data

Feb. 23, 2001 (EP) .................. 01103662
Jul. 20, 2001 (EP) .................. 01116782

(51) Int. Cl.
*C07D 241/04* (2006.01)
*C07D 209/44* (2006.01)
*A61K 31/4965* (2006.01)
*A61K 43/38* (2006.01)

(52) U.S. Cl. .................. 514/255.01; 514/415; 544/386; 548/482

(58) Field of Classification Search ................ 544/386; 548/482; 514/255.01, 415
See application file for complete search history.

(56) References Cited

U.S. PATENT DOCUMENTS 6,794,507 B2 * 9/2004 Cappi et al. ................ 544/386

* cited by examiner

*Primary Examiner*—Zachary C. Tucker
*Assistant Examiner*—Ebenezer Sackey
(74) *Attorney, Agent, or Firm*—Peter F. Corless; Jeffrey D. Hsi; Edwards Angell Palmer & Dodge LLP

(57) ABSTRACT

The present invention relates to compounds of the Formula

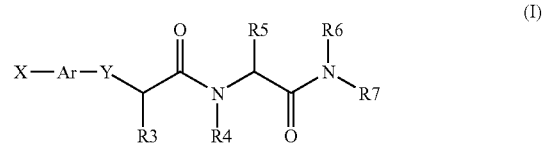

or a pharmaceutically acceptable salt, solvate, hydrate or formulation thereof. These compounds can be used for the inhibition of Factor Xa and for the treatment and/or prevention of diseases that are mediated by Factor Xa activity.

10 Claims, No Drawings

COMPOUNDS THAT INHIBIT FACTOR XA ACTIVITY

The present invention relates to novel compounds, their pharmacologically acceptable salts, or solvates and hydrates, respectively, and to pharmaceutical compositions containing the same as active ingredient that are capable to inhibit Factor Xa activity in vivo. These novel compounds are potent Factor Xa inhibitors which makes them useful for the prevention and/or treatment of thrombolytic disorders and other diseases that are mediated by factor Xa activity. The present invention furthermore relates to prodrugs, optically active forms, racemates and diastereomers of such compounds and salts.

Factor Xa is a trypsin-like serine proteinase that converts the prothrombin zymogen to its active form, thrombin. Unlike thrombin, which is known to act on several protein substrates, Factor Xa specifically cleaves prothrombin at two sites, both adjacent to arginine residues. Human Factor Xa is an essential component of the prothrombinase complex and leads to the formation of thrombin. Thus, the inhibition of factor Xa represents an important strategy in the development of new antithrombotic drugs. Factor Xa plays a central role in the coagulation pathway since it is part of the common pathway of both the intrinsic and extrinsic coagulation systems.

It is an object of the present invention to provide novel compounds exhibiting useful properties, in particular Factor Xa inhibiting activity. It is another object of the present invention to provide suitable pharmaceutical compositions. Moreover, it is desired that these new compounds are capable of being utilized in the prevention and/or treatment of diseases which involve Factor Xa activity.

The present invention describes compounds, their pharmacologically acceptable salts, or solvates and hydrates, respectively and formulations that are new and exhibit high activity and selectivity. The present invention furthermore relates to pro-drugs, optically active forms, racemates and diastereomers of such compounds and salts. These compounds and salts may, in turn, be pro-drugs which will be metabolically activated. The present invention furthermore describes pharmaceutical compositions containing said compounds and salts, respectively, as active ingredient. Furthermore, the use of such active ingredients in the prevention and/or treatment of diseases which involve Factor Xa activity is disclosed. Furtheron, the compounds of the present invention are potent inhibitors of other serine proteases like Factor VIIa, Factor IX, tryptase and urokinase (uPA) which makes them useful for the treatment and/or prevention of diseases which involve tryptase and/or urokinase activity like allergic diseases, inflammatory diseases or cancer.

The present invention provides compounds of Formula (I):

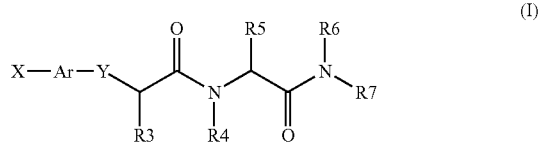

wherein

X is H, Cl, Br, —C(=NR1)NH$_2$, —CH$_2$NH$_2$, —NH—C(=NR1)NH$_2$, —S—C(=NR1)NH$_2$, —NH—C(=NH)—C(=NH)NH$_2$, —C(=NH)SR1, —NH$_2$, —C(=N—NH$_2$)NH$_2$, wherein R1 is —H, —OH, —C(=O)OR2, alkyl, aralkyl, aralkyloxy, aryloxy or a heteroalkyl group, such as alkoxy, acyl or acyloxy, wherein R2 is alkyl, heteroalkyl, a carbocycle, heterocycloalkyl, aryl, heteroaryl or aralkyl;

Y is O, S, SO, SO$_2$, SO$_2$NH, PO$_2$NH, NR10, CO or CR8R9 wherein R8, R9 and R10 are independently H, alkyl, heteroalkyl, carbocycle, heterocycloalkyl, aryl, heteroaryl, aralkyl or heteroarylalkyl with the exception, that if Y is NR10, X is not —(=NR1) NH$_2$;

Ar is aryl, heteroaryl, heteroarylalkyl or aralkyl wherein X is directly attached to the aromatic ring system;

R3 is H, an alkyl group, a heteroalkyl group, a carbocycle, a heterocycloalkyl group, an aryl group, a heteroaryl group, a heteroarylalkyl group or an aralkyl group;

R4 is H, alkyl, heteroalkyl, a carbocycle, heterocycloalkyl, aryl, heteroaryl, heteroarylalkyl or aralkyl;

R5 is H, an alkyl group, a heteroalkyl group, a carbocycle, a heterocycloalkyl group, an aryl group, a heteroaryl group or an aralkyl group and R6 and R7 are independently H, alkyl, heteroalkyl, a carbocycle, heterocycloalkyl such as aryl-heterocycloalkyl, aryl, heteroaryl, aralkyl or heteroarylalkyl or are together members of a heterocycloalkyl ring system, in particular an aryl-heterocycloalkyl ring system, or a heteroaryl ring system, which systems may be substituted with one or more preferably unsubstituted groups selected from alkyl, heteroalkyl a carbocyclic group, heterocycloalkyl, aryl, heteroaryl, aralkyl, heteroarylalkyl, —OH or —NH$_2$;

or a pharmacologically acceptable salt, solvate, hydrate or formulation thereof.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more asymmetric or chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

The following more specific definitions for general substituents apply throughout the description and the claims and in any combination.

The term alkyl refers to a saturated or unsaturated (i.e. alkenyl and alkinyl) straight or branched chain alkyl group, containing from one or two to ten carbon atoms, preferably from one or two to six carbon atoms, e.g. 1, 2, 3 or 4 carbon atoms, for example methyl, ethyl, propyl, iso-propyl, butyl, iso-butyl, tert.-butyl, n-hexyl, 2,2-dimethylbutyl, noctyl; ethenyl (vinyl), propenyl, iso-propenyl, butenyl, isoprenyl or hexa-2-enyl; ethinyl, propinyl or butinyl groups. The alkenyl or alkinyl groups contain preferably one or two double and/or triple bounds.

The term heteroalkyl refers to an alkyl group as defined herein where one, two or more carbon atoms are replaced by an oxygen, nitrogen, phosphorous or sulphur atom, especially by an oxygen and/or nitrogen atom for example: alkoxy groups, such as $C_1$-$C_4$-alkoxy groups, like methoxy, ethoxy, propoxy, isopropoxy, butoxy or tert.-butoxy; a (1-4C)alkoxy(1-4C)alkyl group such as methoxymethyl, ethoxymethyl, 1-methoxyethyl, 1-ethoxyethyl, 2-methoxyethyl or 2-ethoxyethyl; or a cyano group; or a 2,3-dioxyethyl group.

The term heteroalkyl furthermore refers to a group derived from a carboxylic acid or carboxylic acid amide containing from one or two to ten carbon atoms, preferably from one or two to six carbon atoms, e.g. 1 or 2 to 4 carbon atoms, and may, for example, be acyl containing e.g. from one to ten carbon atoms, preferably from one to six carbon atoms, e.g. 1 to 4 carbon atoms, such as acetyl, propionyl, butyryl or pivaloyl; acyloxy containing e.g. from one to ten carbon atoms, preferably from one to six carbon atoms, e.g. 1 to 4 carbon atoms such as acetyloxy, propionyloxy, butyryloxy or pivaloyloxy; carboxyalkyl containing from one to ten carbon atoms, preferably from one to six carbon atoms, e.g. 1 to 4 carbon atoms such as carboxymethyl, carboxyethyl, carboxypropyl, carboxybutyl, carboxyalkyl ester containing from one to ten carbon atoms, preferably from one to six carbon atoms, e.g. 1 to 4 carbon atoms, such as carboxyalkyl methyl ester, carboxyalkyl ethyl ester, carboxyalkyl propyl ester, carboxyalkyl isopropyl ester, carboxyalkyl butyl ester or carboxyalkyl tert.-butyl ester, carboxyalkyl amide or alkylcarbamoyl such as N-(1-4C)alkylcarbamoyl or N,N'-(1-4C)dialkylcarbamoyl) containing from one to ten carbon atoms, preferably from one to six carbon atoms, e.g. 1 to 4 carbon atoms such as N-methylcarbamoyl, N-ethylcarbamoyl, N-propylcarbamoyl, N,N'-dimethylcarbamoyl, N-ethyl-N-methylcarbamoyl or N,N'-dipropylcarbamoyl, alkoxycarbonyl containing from one to ten carbon atoms, preferably from one to six carbon atoms, e.g. 1 to 4 carbon atoms, such as methoxycarbonyl, ethoxycarbonyl, propoxycarbonyl, isopropoxycarbonyl, butoxy- or tert.-butoxycarbonyl or alkoxycarbonyloxy containing from one to ten carbon atoms, preferably from one to six carbon atoms, e.g. 1 to 4 carbon atoms such as methoxycarbonyloxy, ethoxycarbonyloxy, propoxycarbonyloxy, isopropoxycarbonyloxy, butoxycarbonyloxy, tert.-butoxycarbonyloxy.

The term carbocyclic group or carbocycle refers to a saturated or partially unsaturated, cyclic or branched cyclic group, having one, two or more rings, preferably one ring formed by a skeleton that contains from 3 to 14 carbon atoms, preferably from five or six to ten carbon atoms, for example cyclopropyl, cyclobutyl, cyclopentyl, cyclohexyl, tetralin, cyclopentenyl or cyclohex-2-enyl groups. The unsaturated carbocyclic groups contain preferably one ore two double and/or triple bonds.

The term heterocycloalkyl refers to a carbocyclic group as defined herein where one, two or more carbon atoms are replaced by one or more oxygen, nitrogen, phosphorous or sulphur atoms, especially by oxygen or nitrogen atoms. Specific examples for heterocycloalkyl are piperidino, morpholino, N-methyl-piperazino, N-phenyl-piperazino, glycosyloxy or glycosyl groups. Preferably one or two carbon atoms are replaced by one or two of the above-mentioned hetero atoms, especially by oxygen and/or nitrogen.

The term aryl refers to an aromatic cyclic or aromatic branched cyclic group, having one, two or more rings, preferably one or two rings, formed by a skeleton that contains from 5 to 14 carbon atoms preferably from five or six to ten carbon atoms, for example phenyl, indenyl or naphthyl groups. Specific examples are a benzyl, tolyl, phenethyl, xylyl, cumyl, 2-, 3- or 4-methoxyphenyl, 2-, 3- or 4-ethoxyphenyl, 4-carboxyphenyl alkyl or 4-hydroxyphenyl group.

The term heteroaryl refers to an aryl group as defined herein where one, two or more carbon atoms, preferably one or two carbon atoms, are replaced by an oxygen, nitrogen, phosphorous and/or sulphur atom, preferably by an oxygen and/or nitrogen atom, for example 4-pyridyl, 2-imidazolyl, 3-pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyridinyl, pyrimidinyl and pyridazinyl groups.

The terms aralkyl and heteroarylalkyl refer to groups that comprise both aryl or, respectively, heteroaryl and alkyl and/or heteroalkyl (for example alkoxy groups as defined above in case of aralkyloxy) and/or carbocyclic and/or heterocycloalkyl ring systems as defined herein, and contain from 1 to 4 rings, preferably 1, 2 or 3 rings, and up to 6 alkyl groups, preferably 0, 1, 2 or 3 alkyl groups. Preferably aralkyl or heteroarylalkyl contain 5 to 20, especially 5 to 10 ring atoms. Examples are the tetrahydroisoquinolinyl, benzyl, 2- or 3-ethyl-indolyl, 2- or 3-glycosyloxy phenyl or 4-methylpyridino groups.

The term glycosyloxy group refers to a saccharide which is linked via an α- or β-O-glycosidic link, especially a monosaccharide, preferred glucose or fructose.

The term glycosyl group refers to a saccharide, especially a monosaccharide, preferred glucose or fructose.

Any alkyl, alkenyl, alkinyl, heteroalkyl, carbocycle, heterocycloalkyl, aryl, heteroaryl, aralkyl or heteroarylalkyl as defined herein may be substituted with one or more, preferably substituents such as F, Cl, Br, I, OH, $NH_2$, SH or $NO_2$-groups or unsubstituted alkyl, heteroalkyl, aryl, aralkyl, aralkyloxy, heteroaryl, carbocylic or heterocycloalkyl groups as defined herein.

Preferred and/or advantageous embodiments of the invention are subject-matter of the subclaims.

Preferred are compounds of Formula (I) as defined herein, wherein X is —C(=NR1)$NH_2$.

More preferred are compounds of Formula (I) as defined herein, wherein R1 is H or an OH, alkoxy e.g. $C_1$-$C_4$ alkoxy like methoxy or ethoxy, aralkyloxy, e.g. benzyloxy or aryloxy, e.g. phenyloxy group.

Moreover preferred are compounds of Formula (I) as defined herein, wherein Y is O or $CH_2$.

Especially preferred are compounds of Formula (I) as defined herein, wherein Ar is m-phenyl which may be unsubstituted or substituted by one, two or more F, OH or OMe groups.

Further preferred are compounds of Formula (I) as defined herein, wherein R3 is an aryl-, e.g. a $C_6$-$C_{10}$ aryl like phenyl, an arylalkyl-, e.g. a $C_7$-$C_{20}$ arylalkyl or a heteroarylalkyl containing, e.g. 6 to 20 C-atoms and 1, 2 or 3 heteroatoms and comprising 1 or 2 rings, or a Ph—O—$CH_2$—COOH, bound in the 2- or 3-position of the phenyl-ring, especially a 2- or 3-glycosyloxy phenyl group.

Further preferred compounds of Formula (I) as defined herein are those compounds in which R4 is H.

Further preferred compounds of Formula (I) as defined herein are those compounds in which R5 is H.

Further preferred are compounds of Formula (I) as defined herein, wherein R6 and R7 are together part of an arylheterocycloalkyl ring system, especially preferred R6 and R7 are together part of a piperazin-ring which is N-substituted with an unsubstituted or substituted aryl ring, wherein aryl especially is a phenyl ring which maybe substituted with one or two F, Cl-atoms or MeO-groups.

The present invention also relates to pharmacologically acceptable salts, or solvates and hydrates, respectively, and to compositions and formulations of compounds of Formula (I). The present invention describes procedures to synthesize the above compounds, to produce pharmaceutically useful agents, which contain these compounds, as well as the use of these compounds for the production of pharmaceutically useful agents.

The pharmaceutical compositions according to the present invention contain at least one compound of Formula I as the active agent and optionally carriers and/or diluents and/or adjuvants.

Examples of pharmacologically acceptable basic salts of compounds of Formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleinic and Salicylic acid. Further, a sufficiently acid compound of Formula (I) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, N-methyl-D-aminomethane (meglumin), piperidine, morpholine, tris-(2-hydroxyethyl)amine, lysine or arginine salts. Compounds of Formula (I) may be solvated, especially hydrated. The hydratisation can occur e.g. during the process of production or as a consequence of the hygroscopic nature of the initially water free compounds of Formula (I). The compounds of Formula (I) can contain asymmetric C-atoms and may be present either as achiral compounds, mixtures of diastereomers, mixtures of enantiomers or as optically pure compounds.

The present invention also relates to pro-drugs which are composed of a compound of Formula (I) and at least one pharmacologically acceptable protective group which will be cleaved off under physiological conditions, such as an alkoxy-, aralkyloxy-, acyl- or acyloxy group as defined herein, e.g. ethoxy, benzyloxy, acetyl or acetyloxy.

A compound, a pro-drug thereof or a pharmaceutical composition of the present invention can be used for the inhibition of Factor Xa, the treatment or prevention of diseases that are mediated by Factor Xa activity, and especially for the treatment of thrombosis, arteriosclerosis, apoplexis, angina pectoris, claudicatio intermittensis and cardiovascular diseases and cancer.

As mentioned above, therapeutically useful agents that contain compounds of Formula (I), their solvates, salts and formulations are also comprised in the scope of the present invention. In general, compounds of Formula (I) will be administered by using the known and acceptable modes known in the art, either alone or in combination with any other therapeutic agent. Such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containg the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use excipients as are e.g. water, alcohols, aqueous saline, aqueous dextrose, polyols, glycerin, vegetable, petroleum, animal or synthetic oils. For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

Combinations with other therapeutic agents may include other therapeutically useful agents, e.g. that are used to prevent or treat asthma and allergic diseases, as are e.g. beta-adrenergic agonists, corticosteroids, methylxanthines, chromoglycates, leucotriene antagonists or histamine antagonists.

For the prevention and/or treatment of the diseases described above the dose of the biologically active compound may vary within broad limits and can be adjusted to the individual needs. In general a dose of 0.1 microgram to 4 milligram per kilogram body weight per day is appropriate, with a preferred dose of 0.5 to 1 or 2 milligram/kilogram per day. In appropriate cases the dose may be also higher or lower than given above.

Compounds of Formula (I) can be synthesized by coupling an acid compound of Formula (II) with an amine compound of Formula (III) in a solvent like dimethylformamide with a coupling reagent like dicyclohexylcarbodiimide and 1-hydroxybenztriazole.

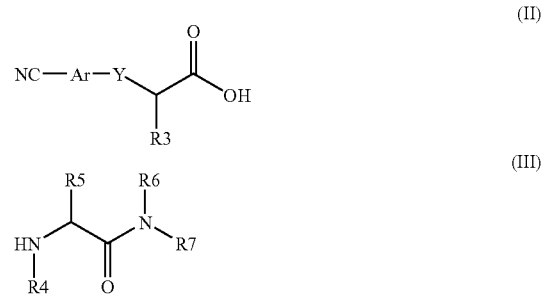

For the conversion of —CN into —C(=NH)NH$_2$ one can dissolve the starting nitrile in a solvent like ethanol or methanol or a solvent mixture as chloroform and methanol or chloroform and ethanol and expose this solution to a stream of water free hydrochloride at a temperature of less than 10 degrees Celsius. The intermediate product is precipitated with ether and filtered off after a reaction time of several hours to days. One can then dissolve this intermediate product in water, and extract it with a solvent like dichloromethane, chloroform or ethyl acetate after neutralisation with a base like sodium carbonate or hydroxide. The obtained material is then reacted with anhydrous ammonia or an ammonia salt like ammonia hydrochloride in a solvent like methanol or ethanol, preferentially at a temperature up to 80 degrees Celsius. Alternatively, one can react the filtered intermediate instantly with anhydrous ammonia or an ammonia salt like ammonia hydrochloride in a solvent like methanol or ethanol. For the conversion of —CN into —C(=NR)NH$_2$, a primary amine is used instead of ammonia.

For the conversion of —CN to —C(=N—OR)NH$_2$ one can dissolve the starting nitrile in a solvent like dimethylformamide or ethanol and add the solution to a reaction mixture of a base like sodium, sodium hydride or triethylamine and hydroxylamine or a hydroxylamine salt like hydroxylamine hydrochloride or a hydroxylamine ether in a solvent like dimethylformamide or ethanol, preferentially at a temperature below 5 degrees Celsius.

Compounds of Formula (I) where R1 is —C(=O)OR2 can be synthesized by reacting a compound of Formula (I) where R1 is H, in a solvent like dimethylformamide or dichloromethane with a chloroformeate of Formula ClC(=O)OR2, the compounds of Formula (I) where R1 is acyl can be synthesized by using the corresponding acyl halides.

Amine compounds of Formula (III) can be synthesized by coupling an N-Boc protected amino acid (IV) with an amine of Formula (V) by using standard coupling methods with a coupling reagent like carbonyldiimidazole or dicyclohexylcarbodiimide and 1-hydroxybenzotriazole.

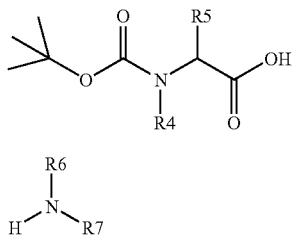

(IV)

(V)

Deprotection of the amine group by treatment with an acid like hydrochloric acid in water or dichloromethane yields the final compounds of Formula (III).

Acid compounds of Formula (II) where Y is O or S can be synthesized by reacting a compound of Formula (VI) where Y is O or S and an alpha-chloro acid of Formula (VII) with a base like sodium hydroxide in water.

NC—Ar—YH (VI)

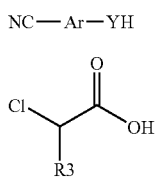

(VII)

Compounds of Formula (II) where Y is SO or $SO_2$ can be synthesized by selectively oxidizing a compound of Formula (II) where Y is S. Compounds of Formula (II) where Y is CHR9 can be synthesized via Palladium-catalyzed hydrogenation of the corresponding cinnamic acid in ethanol (eg. Wagner G. et al, Pharmazie 1973, 28, 724-729).

In the following the invention is described in more detail with reference to examples. These examples are intended for illustration only and are not to be construed as any limitation.

EXAMPLES

The enzyme assay war carried out at room temperature in Tris HCl buffer (pH: 8 consisting of 100 mM Tris HCl, 100 mM NaCl, 0.1% PEG 6000 and 0.05% Tween 80) in 384-well microtiter plates in a total volume of 50 µl with a final enzyme conc. of 3 nM. Compound dilutions (5 µl each in 50% DMSO/50% water) were added to the wells containing buffer and enzyme and preincubated for 10 min. The enzymatic reaction was initiated by the addition of substrate (final concentration of 150 µM). The color developed from the release of p-nitroanilide from the chromogenic substrate was monitored continuously for 20 min. at 405 nm using the SPECTRA FLUOR PLUS microtiter plate reader (Tecan, Crailsheim). The initial velocities measured were used to determine the amount of inhibitor required to diminish 50% of the control velocity and defined as the IC50 of the inhibitor by using the programm Grafit (Erythacus Software Ltd.). Assuming that the kinetic mechanisms were competitive inhibition, the apparent Ki values could then be calculated according to the Cheng-Prusoff equation: $K_i=IC_{50}/(1+[S]/Km)$, (Y.-C. Cheng, W. H. Prusoff, Biochemical Pharmacology, Vol. 22, pp. 3099-3108, Pergamon Press, 1973).

To show the inhibition of the catalytic activity of Factor Xa one may use chromogenic peptide substrates. The inhibition of the amidolytic activity of Factor Xa by the compounds described above was shown as follows. The measurements were carried out at room temperature in microtiter plates. The compounds were dissolved in dimethylsulfoxide and 5 µl of varying concentrations of the compounds were added to a 100 nM solution of human recombinant Factor Xa in a buffer (pH: 8.0 using 50 mM Tris-HCl, 100 mM NaCl, 0.1% PEG 6000, 0.05% Tween 80). Finally 200 µM of N-Methoxycarbonyl-D-norleucyl-glycyl-L-arginine-4-nitrani-lide acetate in buffer were added and the hydrolysis of the substrate was followed with a spectrophotometer. The inhibitory constants ($K_i$) were determined according to the method described in Biochem. J. 55, 1955, 170-171.

The examples that were tested showed $IC_{50}$'s in between 0.1 and 20 µM range.

Example 1

2-(3-Carbamimidoyl-phenoxy)-N-{[2-(1H-indol-3-yl)ethylcarbamoyl]-methyl}-acetamide 48.5 g (303 mmol) tryptamine were reacted with 100 g (303 mmol) Cbz-Gly-ONp (Np=p-nitro-phenyl) in ethyl acetate. The deprotection of the Cbz-group was carried out in a mixture of DMF and THF using 10 g Pd/C 10% and hydrogen yielding 50 g (231 mmol, 76%) of the desired amine 1.

5.955 g (50 mmol) 3-cyanophenol, 4.725 g (50 mmol) chloroacetic acid, 4 g (100 mmol) sodium hydroxide and 2.5 mL water were mixed and stirred under reflux. After 6 hours the mixture was neutralized with hydrochloric acid and extracted with ether. The organic phase was extracted with aquaeous sodium bicarbonate. The water phase was neutralized with hydrochloric acid an the resulting precipitate was filtered off to give 4.066 g (23 mmol, 46%) of the desired acid 2.

266 mg (1.5 mmol) acid 2, 229 mg (1.5 mmol) HOBt and 309 mg (1.5 mmol) DCC were dissolved in 20 mL DMF and stirred at room temperature. After 30 minutes, 459 mg (2.1 mmol) amine 1 were added and the mixture was stirred at room temperature overnight. Ethyl acetate was added and the mixture was washed with aqueous sodium bicarbonate. The organic phase was dried and the solvent removed under reduced pressure. The residue was dissolved in 15 mL chloroform and 7.5 mL of a saturated solution of hydrogen chloride in anhydrous methanol were added and left at 4° C. for two days. After evaporating the solvents under reduced pressure, 30 mL of an anhydrous solution of ammonia in methanol were added and the mixture was stirred for 4 hours under reflux. The desired product was purified by MPLC to yield 20 mg (0.051 mmol, 3%)

Molecular weight ($C_{21}H_{23}N_5O_3$): 393.4492 MS (ESI): m/z=394 [M+H]

Example 2

2-(3-Carbamimidoyl-phenoxy)-N-{[2-(1H-indol-3-yl)ethylcarbamoyl]-methyl}-propionamide In analogy to example 1 using 3-bromopropionic acid, 470 mg (1.153 mmol) of the desired product were obtained.

Molecular weight ($C_{22}H_{25}N_5O_3$): 407.4763 MS (ESI): m/z=408 [M+H]

Example 3

2-(3-Aminomethyl-phenylamino)-N-{[2-(1H-indol-3yl)-ethylcarbamoyl]-methyl}-propionamide An acid-compound, which was prepared by reductive amination from 3-cyanoaniline and pyruvic acid, was coupled with DCC and HOBt in DMF to an amine compound which was prepared from tryptamine and Cbz-Gly-ONp (Np=p-nitrophenyl) by coupling in ethyl acetate and subsequent deprotection of the Cbz-group with hydrogen and Pd/C as catalyst in a mixture of DMF and THF.

The cyanide was transformed into the amine, by reduction with hydrogen using 10% Pd/C as catalyst in methanol.

Molecular weight ($C_{22}H_{27}N_5O_2$): 393.49 MS (ESI): m/z=394 [M+H]

Example 4

3-(3-Carbamimidoyl-phenyl)-N-{[2-(1H-indol-3-yl)ethylcarbamoyl]-methyl}-2-methyl-propionamide An acid compound which was prepared from 4-cyanobenzaldehyde and propionic anhydride using sodium propionate (G. Werner et al. Chem. Ber. 1895, 28, 1997-2002) and subsequent reduction of the double bond with hydrogen using Pd/C as catalyst in ethanol was coupled with DCC and HOBt in DMF to an amine compound which was prepared from tryptamine and Cbz-Gly-ONp (Np=p-nitrophenyl) by coupling in ethyl acetate and subsequent deprotection of the Cbz-group with hydrogen and Pd/C as catalyst in a mixture of DMF and THF.

The conversion of the cyanide to the amidine (Pinner-Reaction) was carried out with hydrogen chloride in anhydrous methanol and chloroform followed by treatment with an anhydrous solution of ammonia in methanol.

Molecular weight($C_{23}H_{27}N_5O_2$): 405.50 MS (ESI): m/z=406 [M+H]

Example 5

3-(5-Carbamimidoyl-2-fluoro-phenyl)-N-{[2-(1H-indol-3-yl)-ethylcarbamoyl]-methyl}-2-methyl-propionamide This compound was prepared in analogy to example 4 using 2-fluoro-5-cyanobenzaldehyde for the preparation of the acid compound.

Molecular weight($C_{23}H_{26}N_5O_2F$): 423.49 MS (ESI): m/z=424 [M+H]

Example 6

3-(5-Carbamimidoyl-2-methoxy-phenyl)-N-{[2-(1H-indol-3-yl)-ethylcarbamoyl]-methyl}-2-methyl-propionamide This compound was prepared in analogy to example 4 using 2-methoxy-5-cyanobenzaldehyde for the preparation of the acid compound.

Molecular weight ($C_{24}H_{29}N_5O_3$): 435.53 MS (ESI): m/z=436 [M+H]

Example 7

3-(3-Carbamimidoyl-4-methoxy-phenyl)-N-{[2-(1H-indol-3-yl)-ethylcarbamoyl]-methyl}-2-methyl-propionamide This compound was prepared in analogy to example 4 using 4-methoxy-5-cyanobenzaldehyde for the preparation of the acid compound.

Molecular weight ($C_{24}H_{29}N_5O_3$): 435.53 MS (ESI): m/z=436 [M+H]

Example 8

3-(3-Carbamimidoyl-4-fluoro-phenyl)-N-{[2-(1H-indol-3-yl)-ethylcarbamoyl]-methyl}-2-methyl-propionamide This compound was prepared in analogy to example 4 using 4-fluoro-5-cyanobenzaldehyde for the preparation of the acid compound.

Molecular weight ($C_{23}H_{26}N_5O_2F$): 423.49 MS (ESI): m/z=424 [M+H]

Example 9

2-(3-Carbamimidoyl-phenoxy)-N-{2-[4-(2-methoxyphenyl)-piperazin-1-yl]-2-oxo-ethyl}-2-phenyl-acetamide This compound was prepared in analogy to example 1 using the corresponding approriate starting materials.

Molecular weight ($C_{28}H_{31}N_5O_4$): 501.59
MS (ESI): m/z=502 [M+H]

Example 10

3-(3-Carbamimidoyl-phenyl)-N-{[2-(1H-indol-3-yl)ethylcarbamoyl]-methyl}-propionamide This compound was prepared in analogy to example 4 using the corresponding approriate starting materials.

Molecular weight ($C_{22}H_{25}N_5O_2$): 391.48 MS (ESI): m/z=392 [M+H]

Example 11

3-[3-(N-Ethoxy-carbamimidoyl)-phenyl]-N-{[2-(1H-indol-3-yl)-ethylcarbamoyl]-methyl}-2-methyl-propionamide This compound was prepared in analogy to example 4 using the corresponding approriate starting materials.

Molecular weight ($C_{25}H_{31}N_5O_3$): 449.56 MS (ESI): m/z=450 [M+H]

Example 12

3-[3-(N-Hydroxycarbamimidoyl)-phenyl]-N-{[2-(1H-indol-3-yl)-ethylcarbamoyl]-methyl}-2-methyl-propionamide This compound was prepared in analogy to example 4 using the corresponding approriate starting materials.
Molecular weight ($C_{23}H_{27}N_5O_3$): 421.50 MS (ESI): m/z=422 [M+H]

Example 13

4-[4-(N-Hydroxycarbamimidoyl)-phenyl]-N-{[2-(1H-indol-3-yl)-ethylcarbamoyl]-methyl}-butyramide This compound was prepared in analogy to example 4 using the corresponding approriate starting materials.
Molecular weight ($C_{23}H_{27}N_5O_3$): 421.50 MS (ESI): m/z=422 [M+H]

Example 14

3-[4-(N-Hydroxycarbamimidoyl)-phenyl]-N-{[2-(1H-indol-3-yl)-ethylcarbamoyl]-methyl}-propionamide This compound was prepared in analogy to example 4 using the corresponding approriate starting materials.
Molecular weight ($C_{22}H_{25}N_5O_3$): 407.48 MS (ESI): m/z=408 [M+H]

The invention claimed is:
1. Compounds of the Formula (I)

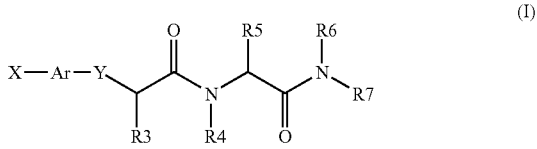

(I)

wherein
X is H, Cl, Br, —C(=NR1)NH$_2$, —CH$_2$NH$_2$, —NH—C(=NR1)NH$_2$, —S—C(=NR1)NH$_2$, —NH—C(=NH)—C(=NH)NH$_2$, —C(=NH)SR1, —NH$_2$, —C(=N—NH$_2$)NH$_2$, wherein R1 is —H, —OH, —C(=O)OR2, alkyl, aralkyl, aralkyloxy, aryloxy or a heteroalkyl group, wherein R2 is alkyl, heteroalkyl, a carbocycle, heterocycloalkyl, aryl, heteroaryl or aralkyl;
Y is O, S, SO, SO$_2$, SO$_2$NH, PO$_2$NH, NR10, CO or CR8R9 wherein R8, R9 and R10 are independently H, alkyl, heteroalkyl, carbocycle, heterocycloalkyl, aryl, heteroaryl, aralkyl or heteroarylalkyl with the exception, that if Y is NR10, X is not —(=NR1)NH$_2$;
Ar is aryl, heteroaryl, heteroarylalkyl or aralkyl wherein X is directly attached to the aromatic ring system;
R3 is H, an alkyl group, a heteroalkyl group, a carbocycle, a heterocycloalkyl group, an aryl group, a heteroaryl, group, a heteroarylalkyl group or an aralkyl group;
R4 is H, alkyl, heteroalkyl, a carbocycle, heterocycloalkyl, aryl, heteroaryl, heteroarylalkyl or aralkyl;
R5 is H, an alkyl group, a heteroalkyl group, a carbocycle, a heterocycloalkyl group, an aryl group, a heteroaryl group or an aralkyl group and
R6 and R7 are independently H, alkyl, heteroalkyl, carbocycle, heterocycloalkyl, aryl, heteroaryl, aralkyl or heteroarylalkyl or are together members of a heterocycloalkyl ring system, or a heteroaryl ring system;
or a pharmacologically acceptable salt, solvate, hydrate, prodrug or formulation thereof.
2. Compounds according to claim 1, wherein X is —C(=NR1)NH$_2$.
3. Compounds according to claim 1, wherein R1 is H or an OH, alkoxy, aralkyloxy or aryloxy group.
4. Compounds according to claims 1, wherein Y is O or CH$_2$.
5. Compounds according to claims 1, wherein Ar is m-phenyl which may be unsubstituted or substituted by one or more F, OH or OMe groups.
6. Compounds according to claims 1, wherein R3 is an aryl-, arylalkyl- or heteroarylalkyl group.
7. Compounds according to claims 1, wherein R4 is H.
8. Compounds according to claims 1, wherein R5 is H.
9. Compounds according to claims 1 wherein R6 and R7 are part of an aryl-heterocycloalkyl ring system.
10. Pharmaceutical compositions containing a compound according to claim 1 as the active agent and optionally carriers and/or adjuvants.

* * * * *